United States Patent [19]

Green

[11] Patent Number: 4,714,187

[45] Date of Patent: Dec. 22, 1987

[54] RELOADING UNIT FOR SURGICAL FASTENING INSTRUMENTS

[75] Inventor: David T. Green, Norwalk, Conn.

[73] Assignee: United States Surgical Corporation, Norwalk, Conn.

[21] Appl. No.: 935,407

[22] Filed: Nov. 26, 1986

[51] Int. Cl.$^4$ ............................................. A61B 17/00
[52] U.S. Cl. .................................. 227/19; 128/334 R; 227/DIG. 1; 227/120; 227/156
[58] Field of Search ....... 128/334 R; 227/19, DIG. 1, 227/120, 156, 136, 135

[56] References Cited

U.S. PATENT DOCUMENTS

| | | | |
|---|---|---|---|
| 3,278,107 | 10/1966 | Rigg | 227/DIG. 1 |
| 4,304,236 | 12/1981 | Conto et al. | 227/DIG. 1 |
| 4,573,622 | 3/1986 | Green et al. | 227/DIG. 1 |

Primary Examiner—Paul A. Bell
Attorney, Agent, or Firm—Kenyon & Kenyon

[57] ABSTRACT

Apparatus for providing a new charge of staples to a staple cartridge in surgical fastening instruments. A transfer magazine, housing the new charge of staples, is adapted to be positioned in alignment with the staple cartridge contained in the instrument. Upon closure of the instrument, a new charge of staples is transferred from the magazine to the staple cartridge thereby allowing for further usage of the instrument.

15 Claims, 9 Drawing Figures

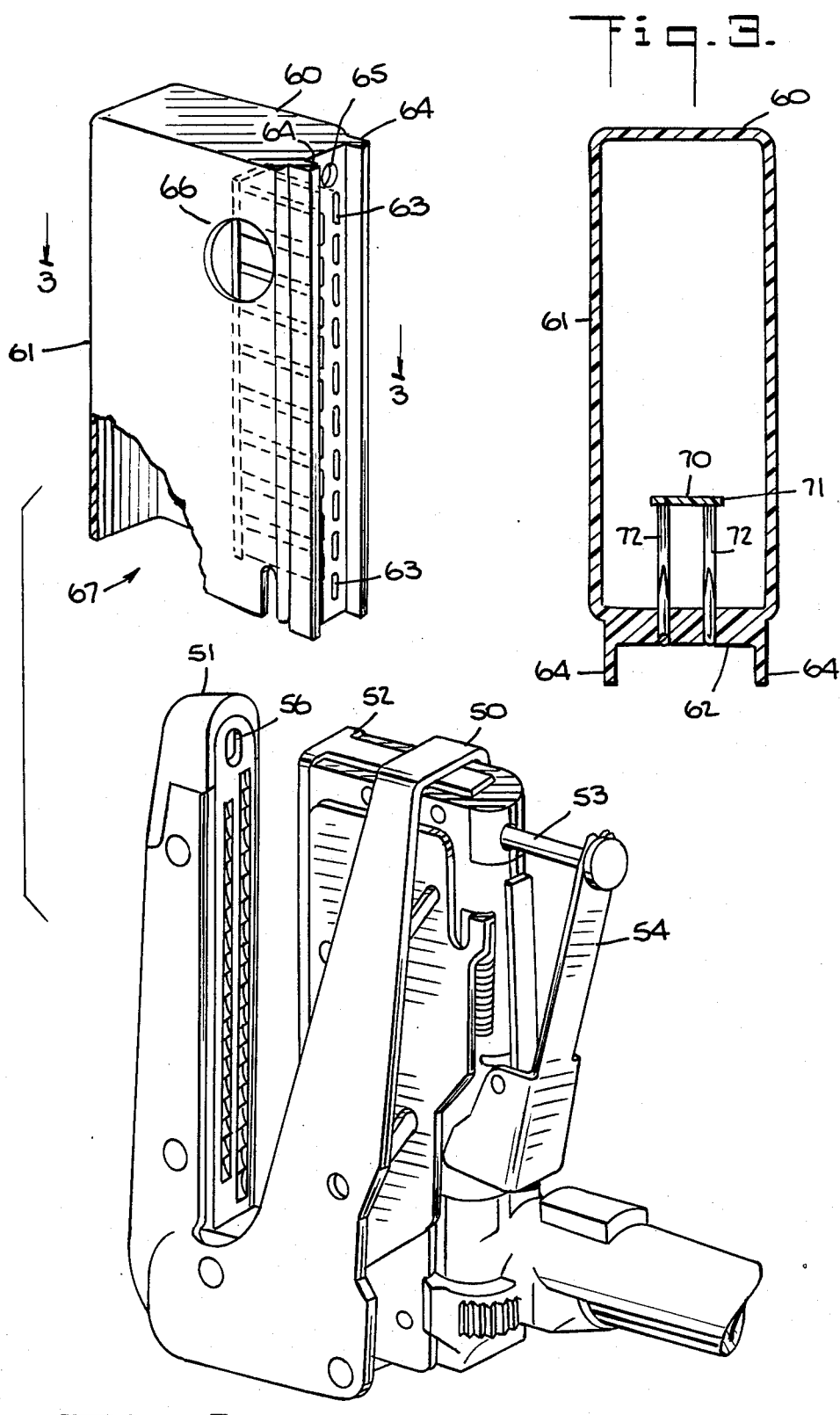

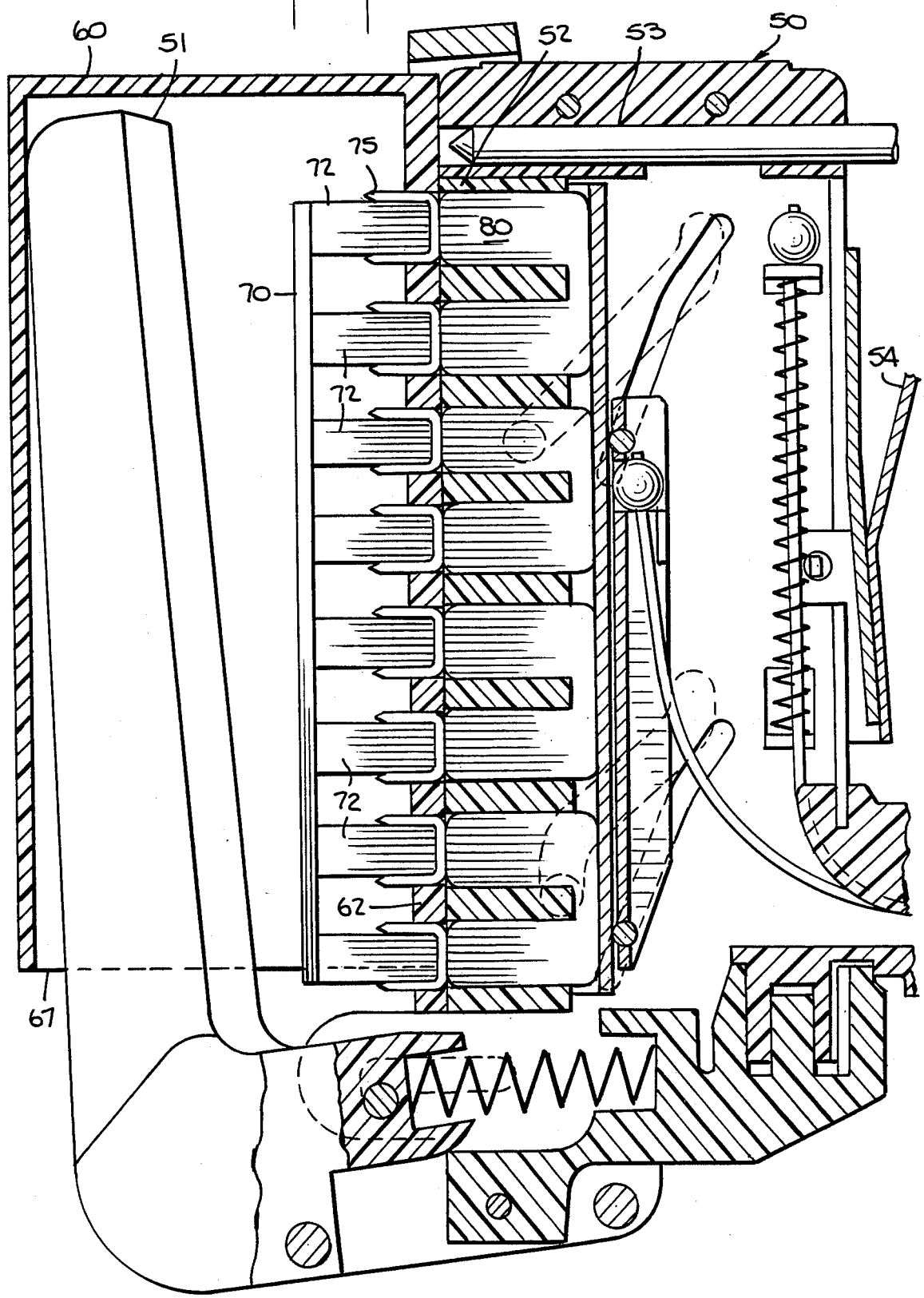

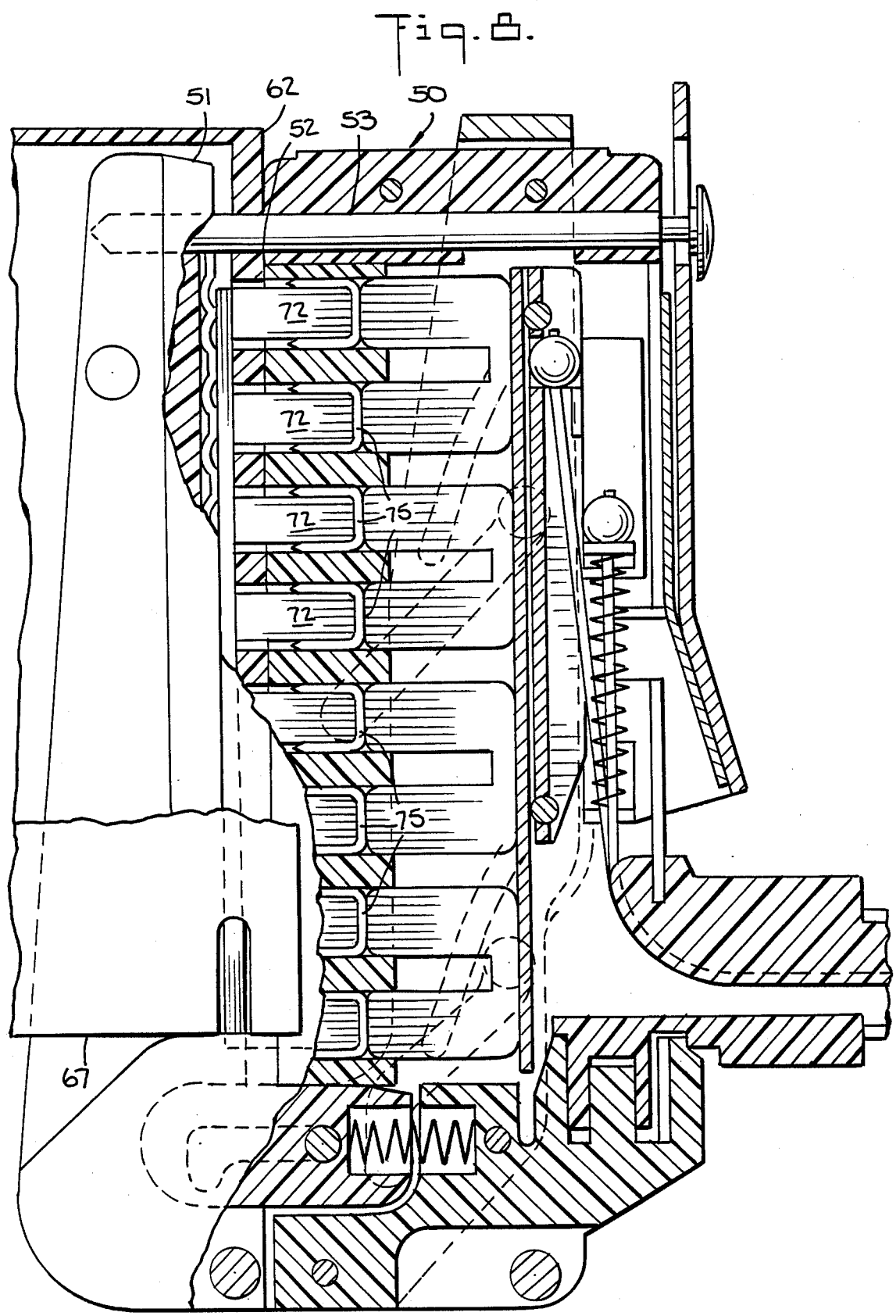

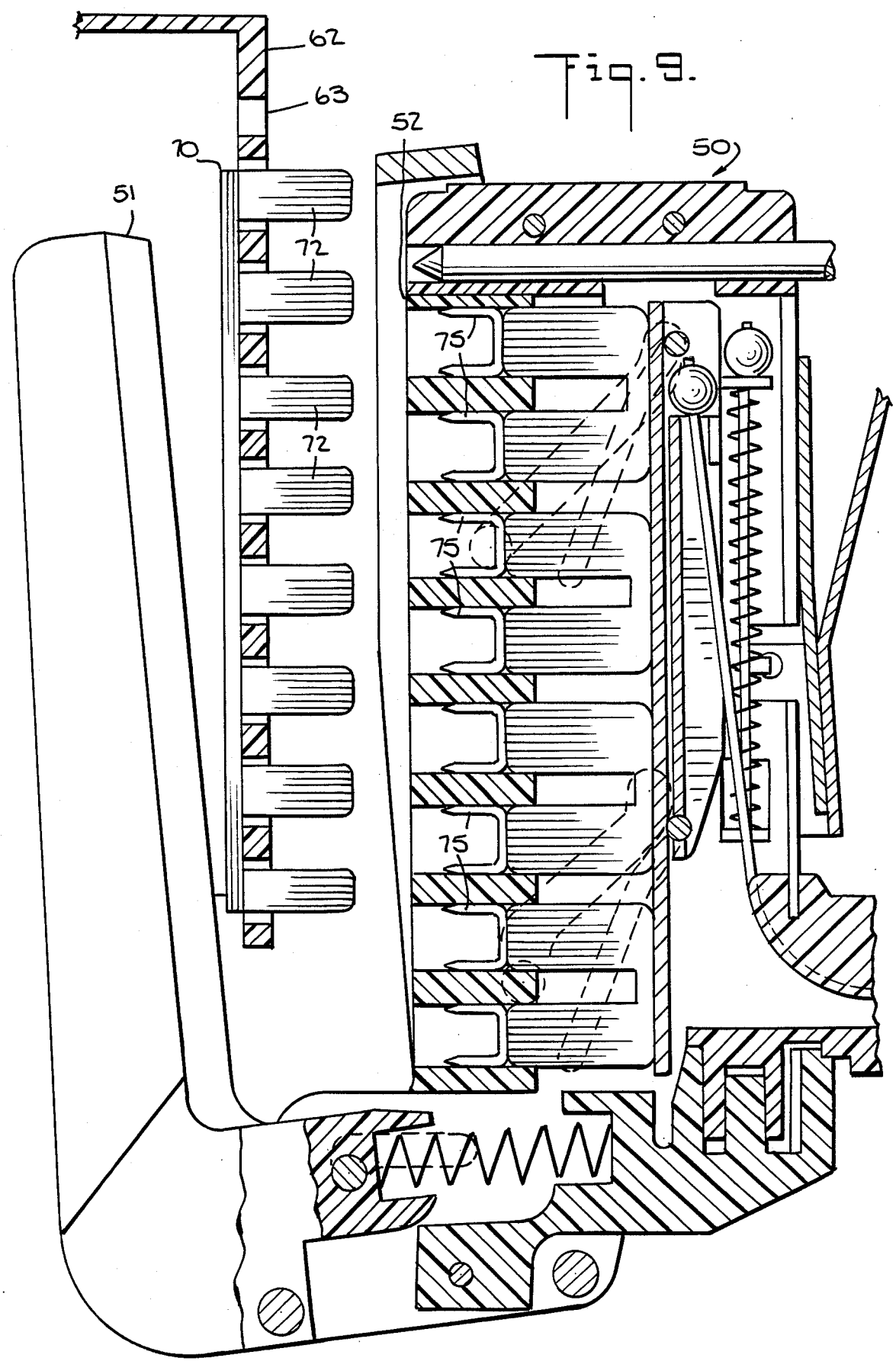

RELOADING UNIT FOR SURGICAL FASTENING INSTRUMENTS

BACKGROUND OF THE INVENTION

This invention relates generally to surgical fastener applying instruments, and more particularly to a reloading unit to facilitate reusing such instruments and their stapling assemblies.

Surgical fastening instruments have been developed utilizing stapling assemblies which include an array or charge of U-shaped staples to be utilized generally simultaneously. Included in the prior art, and illustrative thereof, are surgical fastening instruments which apply linear arrays of staples to body tissue clamped between a staple cartridge and anvil of a stapling assembly. In addition, surgical fasteners known in the prior art apply circular arrays of surgical staples to hollow body organs clamped between the staple cartridge and anvil. Illustrative of the former is U.S. Pat. No. 4,577,322 issued to Green et al. on Mar. 4, 1986, while the latter type instrument is illustrated in U.S. Pat. No. 4,304,236 issued to Conta et al., on Dec. 8, 1981.

While surgical fasteners of the above type have met with a great commercial acceptance, their usage has been limited to a single firing or discharge of an array of staples during a surgical procedure. Once these instruments have been so used, they are typically disposed of, and if another stapling procedure is required during the surgical procedure with the same patient, another instrument is employed. Such usage is expensive since the instrument is used only once and discarded.

Surgical fastening instruments are also available which are intended to be reused, thus providing multiple applications of surgical fastening. In such instruments, after the initial discharge of staples has taken place during a surgical procedure, reuse of the instrument is facilitated by replacing the entire stapling assembly. In other words, the stapling assembly, which includes the staple cartridge and anvil and which may also include an alignment means, is replaced. Thus, the spent stapling assembly is removed from the instrument and a new sterilized stapling assembly is inserted as a replacement therefor.

Staple assemblies are relatively expensive and replacement of numerous staple cartridges or staple assemblies during a single surgical procedure for certain applications become expensive and time consuming.

By the means disclosed herein, a reloading unit for surgical fasteners is provided which facilitates reuse of the instrument several times during a surgical procedure with the same patient. The reloading unit is further advantageous because of its relatively low cost and ease of reloading an otherwise disposable surgical fastener.

SUMMARY OF THE INVENTION

Briefly stated, the invention disclosed herein provides a reloading unit in the form of a transfer magazine for a surgical fastening apparatus which facilitates the multiple use of such apparatus. The reloading unit includes a new charge or array of staples or fasteners and may be utilized in conjunction with arrays of both linear and circular surgical fasteners. The reloading unit may also be used to reload staple cartridges with singular or multiple rows of staples. The transfer magazine is thus adapted to provide a new charge of staples to the staple cartridge and includes along therewith a pusher means and cooperative holding means. The pusher means includes a plurality of spaced apart staple support members each of which is generally shaped to conform to the inner surface of a staple. Over each of the support members is disposed a staple which typically is U-shaped. A holding means, which includes a plurality of spaced receptacles, is adapted to mate with and hold the staples on the support members prior to transfer to the staple cartridge. The holding means is slidably engaged with the staples on the support members of the pusher means and is adapted to release the staples held therein and facilitate loading of a charge of staples into a staple cartridge of a surgical stapling or fastening instrument.

An important requirement with respect to the support members disposed along the pusher means resides in the length of the particular members. In this respect, the length of the support members must be sufficient to properly load the staples into the staple cartridge. It is thus preferred that the staple support members be of a length sufficient to insert and load the staples into the previously used staple cartridge to a depth where the staple ends do not protrude from the surface of the staple cartridge. As can be appreciated, this loading is required to avoid any tearing or cutting of body tissue being inserted between the recharged staple cartridge and the anvil of the newly loaded stapling assembly.

In the preferred embodiment, the pusher member is provided in the form a comb-like bar with the staple support members extended from the interconnecting rear bar portion. The rear bar member thus acts as a stop and limits the extent to which the staples and support members pass through the receptacles in the holding means. In addition, positioning and alignment means are provided for loading and engaging the transfer magazine with the staple cartridge of the surgical fastener. In this respect, a pair of guide rails are provided on the holding means which slidably engage the respective outer sides of the staple cartridge. The receiving means includes an aperture for mating with an alignment pin on the stapling assembly of the surgical instrument. In this manner, the transfer magazine is loaded into the spent stapling assembly, being guided into alignment with the staple cartridge by means of the guide rails provided on the holding means. Alignment is achieved and maintained by passing an alignment pin, provided with the stapling assembly, through an aperture in the transfer magazine. Thus, the new charge of staples in the transfer magazine, which is aligned with the receptacles in the spent staple cartridge, may be transferred into the cartridge upon closure of the instrument.

The preferred embodiment further includes a housing or closure for the transfer magazine. An indicator opening is further provided in the housing to allow viewing of the pusher means. In this manner, one may readily ascertain whether or not a new charge of staples exists within the transfer magazine.

The method of practicing the invention includes the firing or discharging of an array of staples in a surgical fastener of the type described above. Thereafter, a new charge of staples is provided in a transfer magazine for loading into the staple cartridge. The transfer magazine includes a plurality of staples substantially corresponding to the number of staples previously carried in the staple cartridge. After the instrument has been fired, it is opened to separate the staple cartridge and anvil portions of the stapling assembly. At that point, the transfer magazine containing the new charge of staples is positioned between the open portions of the stapling assembly. The transfer magazine is aligned with the staple cartridge to facilitate transfer of the staples from the magazine to the cartridge with the closed end of the U-shaped staple first entering the empty receptacles in the cartridge. Such staple insertion thus aligns the legs of the staple with the opening in the cartridge. Transfer of the staples is accomplished by closing the stapling assembly of the surgical instrument sufficient to close the cartridge and anvil upon the transfer magazine thereby effecting a transfer of the staples from the transfer magazine into the empty receptacles in the staple cartridge.

In the preferred embodiment of the invention, the step of aligning includes utilization of a pin disposed on the stapling assembly to align the transfer magazine therewith by extending the pin through an aperture in the transfer magazine upon closure of the instrument. In addition, positioning of the transfer magazine with respect to the staple cartridge is accomplished by guiding the transfer magazine by means of rail members disposed along the sides thereof so as to slidably engage the spent staple cartridge.

The closing step in the preferred embodiment includes the step of urging the pusher member in the transfer magazine against the inner portion of the staples such that during the step of closing, the pusher member causes the staples to be transferred from the transfer magazine to the empty opening in the staple cartridge. As discussed, it is important that during the closing step the staples are fully inserted into the staple cartridge sufficient to prevent the protrusion of the staple ends through the surface of the newly loaded cartridge.

While the reloading unit of the present invention is illustrated as being adapted for use with a linear surgical fastening instrument, it may also be used to reload staple cartridges having a circular array such as those used, for instance, in an end-to-end anastomosis device. Also, the reloading unit may be used with other linear staple arrangements such as, for instance, a lateral anastomosis stapler of the type described in U.S. Pat. No. 3,499,591.

It is, accordingly, an object of this invention to provide a reloading unit for use in conjunction with surgical fastening instruments to allow for multiple firings thereof.

It is also an object of this invention to provide a reloading unit which permits multiple uses of a surgical fastening instrument and which is relatively inexpensive and simple to use, thus resulting in a substantial reduction of cost when multiple fastening procedures are employed on a patient.

It is a further object of this invention to provide a surgical fastening instrument and reloading unit suitable for use therewith to facilitate multiple uses of the instrument with rapid and effective reloading during a surgical procedure.

These and other objects, advantages and features of the invention will become more apparent from the following description taken in conjunction with the accompanying drawings.

BRIEF DESCRIPTION OF THE DRAWINGS

FIG. 2 is a perspective view of the stapling assembly of a surgical fastening instrument and the reloading unit of the present invention;

FIG. 3 is a top cross-sectional view of the reloading unit of the present invention taken in cross-section along the lines 3—3 of FIG. 2;

FIG. 7 is a side elevation view similar to that of FIG. 6, with the reloading unit of the present invention positioned within the stapling assembly;

FIG. 8 is a side elevation view similar to FIG. 6 & 7, depicting the stapling assembly and reloading unit in the closed reloaded position; and FIG. 9 is a side elevation view similar to that of FIGS. 6, 7, & 8, depicting the reloaded open stapling assembly with the reloading unit being removed therefrom.

DESCRIPTION OF THE PREFERRED EMBODIMENT

The reloading unit of the present invention is described for use in connection with a linear surgical fastening instrument of the type described in U.S. Pat. No. 4,573,622. Thus, the reloading unit depicted herein includes an array of longitudinal U-shaped staples. When used in conjunction with instruments having staple arrays in other forms, such as circular, as described in U.S. Pat. No. 4,304,236, the reloading unit is provided with a comparable shaped array of staples, such as, for instance, a circular array. The reloading unit may also be provided with single or multiple rows of staples depending upon the type of surgical fastening instrument which is to be reloaded.

Figure 1:
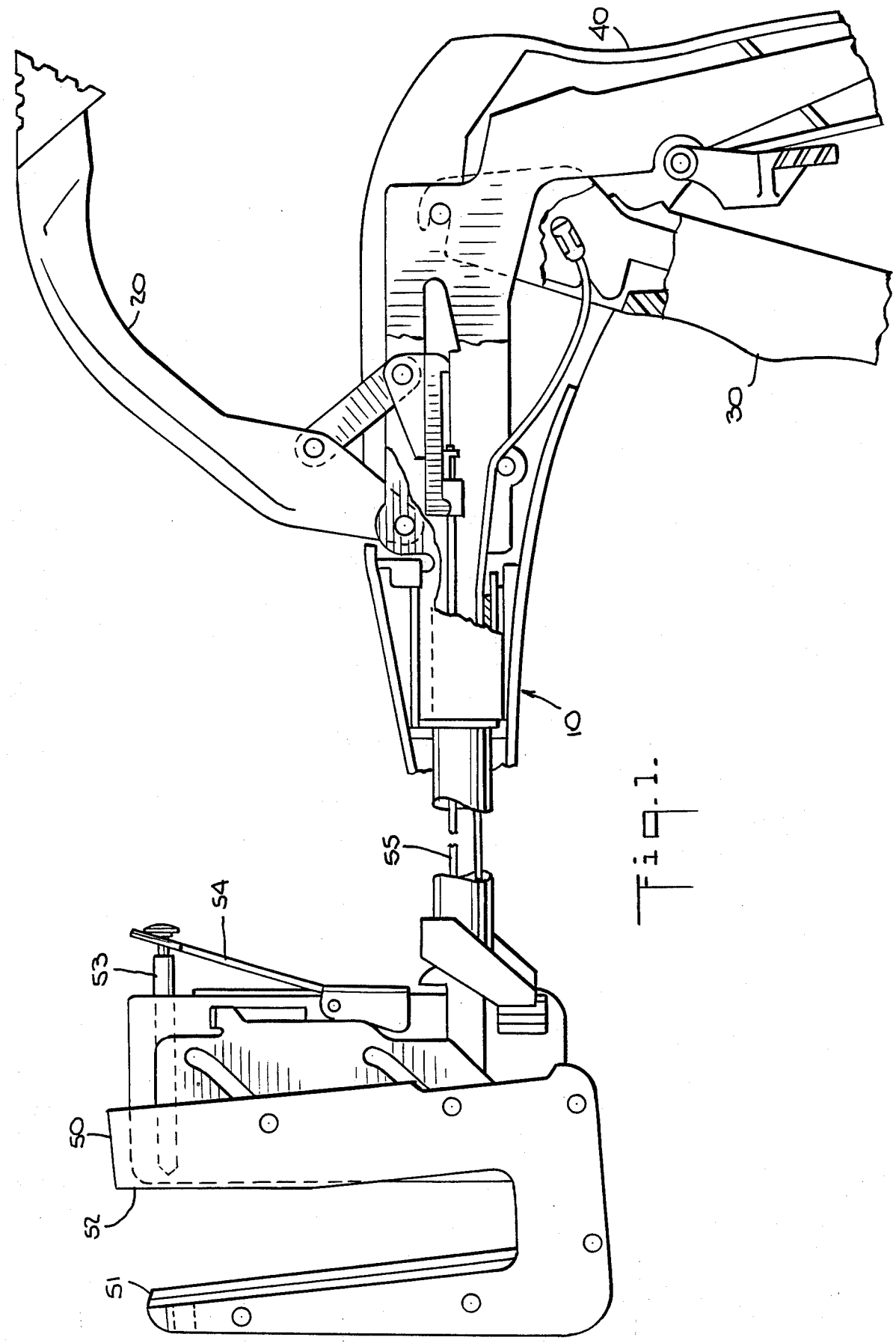
FIG. 1 is a side elevation view, partially in cross-section, of a surgical fastening instrument suitable for use with the reloading unit of the present invention.
Figure 4:
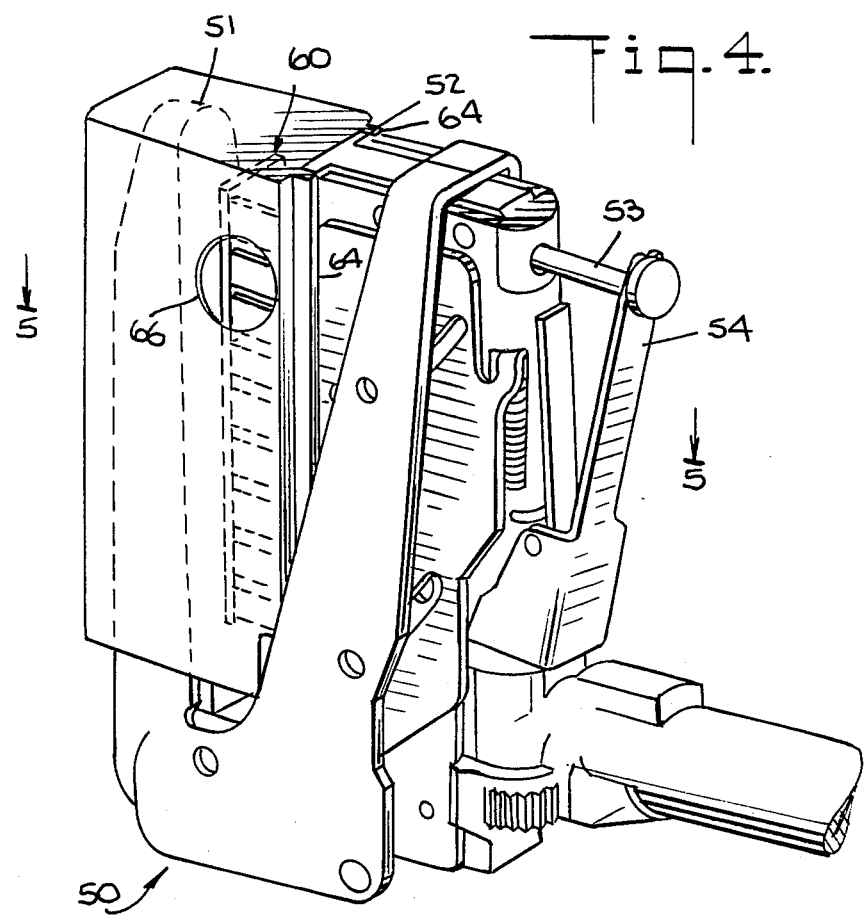
FIG. 4 is a perspective view of a stapling assembly having the reloading unit of the present invention inserted therein.
Figure 5:
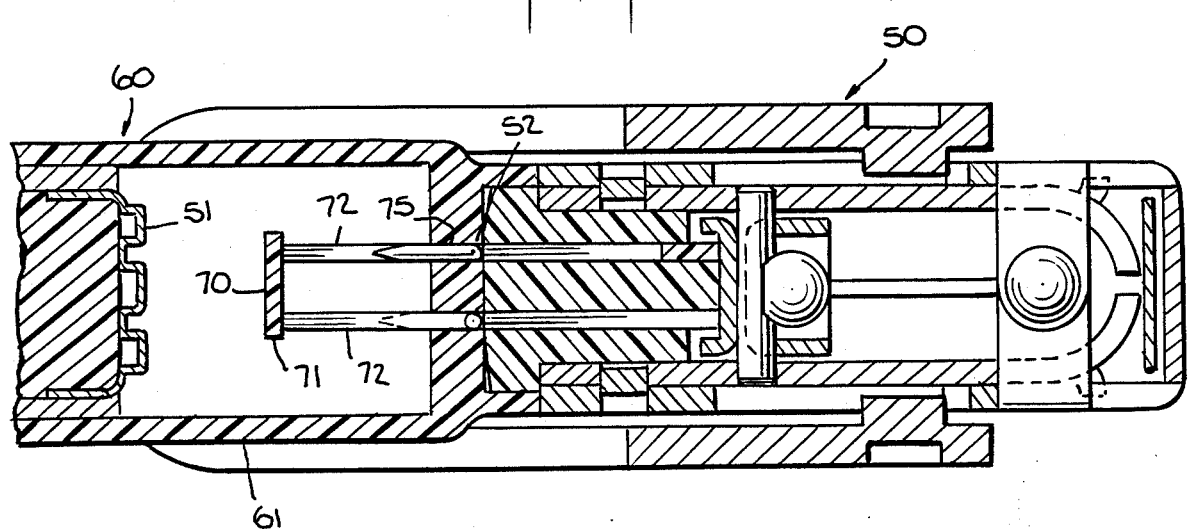
FIG. 5 is a top cross-sectional view taken along the lines 5—5 of FIG. 4.

With reference to the drawings and particularly FIGS. 1 & 2, the linear surgical fastening instrument 10 includes a manually operated clamp actuator lever 20 and a manually operable fastener actuator lever or trigger 30 adjacent to handle portion 40 of the instrument. At the other end of the instrument 10 is a stapling assembly 50 which includes an anvil portion 51 and a staple cartridge 52. A resiliently biased alignment pin 53 is urged toward the open position by means of lever spring 54 which is coupled to the clamp actuator lever 20 by means of longitudinal bar 55.

While the details of the structure and operation of the surgical fastening instrument 10 are described in the U.S. Pat. No. 4,573,622, the disclosure of which is incorporated herein by reference, its overall operation is described with reference to the above identified parts. In this connection, manual closure of clamp actuator 20 causes bar 55 to move forward and move the anvil portion 51 and staple carrying portion 52 with respect to one another. In a surgical procedure, such closure clamps the body tissue therebetween for fastening which is accomplished by squeezing the trigger 30. Closure of clamp actuator 20 also moves the spring lever 54 towards the stapling assembly 50. In this manner, alignment pin 53 is inserted into the receptacle 56 provided in the anvil portion 51 of the stapling assembly 50.

With reference to FIGS. 2 & 3, the reloading unit 60 of the present invention includes a housing portion 61 extending rearwardly from the staple holding plate 62.

Holding plate 62 includes a plurality of apertures 63 through which engage the staples 75 and hold each staple on the support members 72 prior to transfer to the staple cartridge 52. In the illustrative embodiment, two rows of apertures 63 are provided. Depending from holding plate 62 are a pair of guide rails 64. An additional aperture 65 is provided in holding plate 62 to receive alignment pin 53 on surgical instrument 10. A pusher bar 70 is provided in the form of a comb-like structure having a rearward bar 71 from which extends a plurality of teeth 72 which pass through apertures 63 in holding plate 62. Teeth 72 of pusher bar 70 are shaped to conform substantially to the inner surface of the U-shaped staples 75 to be loaded into the staple cartridge 52. Thus, teeth 72 function as support members for the U-shaped staples 75, both of which are slidably movable with respect to holding plate 62. Rearward bar 71 serves as a stop member, and limits the movement of pusher bar 70 with respect to holding plate 62.

Housing 61 includes an opening 66 in at least one wall thereof through which staples 75 being supported on pusher bar 70 may be viewed. In this manner, it may readily be determined whether or not the reloading unit 60 includes a fresh charge of staples 75. Housing 61 also includes open end 67 which is adapted to be inserted over anvil portion 51 when the reloading unit 60 is utilized. It is noted that housing portion 61 may alternatively be provided as a removable member.

After surgical fastening instrument 10 has been fired and the initial load of staples provided with the instrument are discharged, reloading unit 60 which is provided therewith in a sterilized package may be used to reload instrument 10. While it is expected that a single reloading unit will typically be used with each surgical fastening instrument thereby allowing for two firings with a single instrument, it is possible to provide additional reloading units which would allow the instrument to be used additional times.

Figure 6:
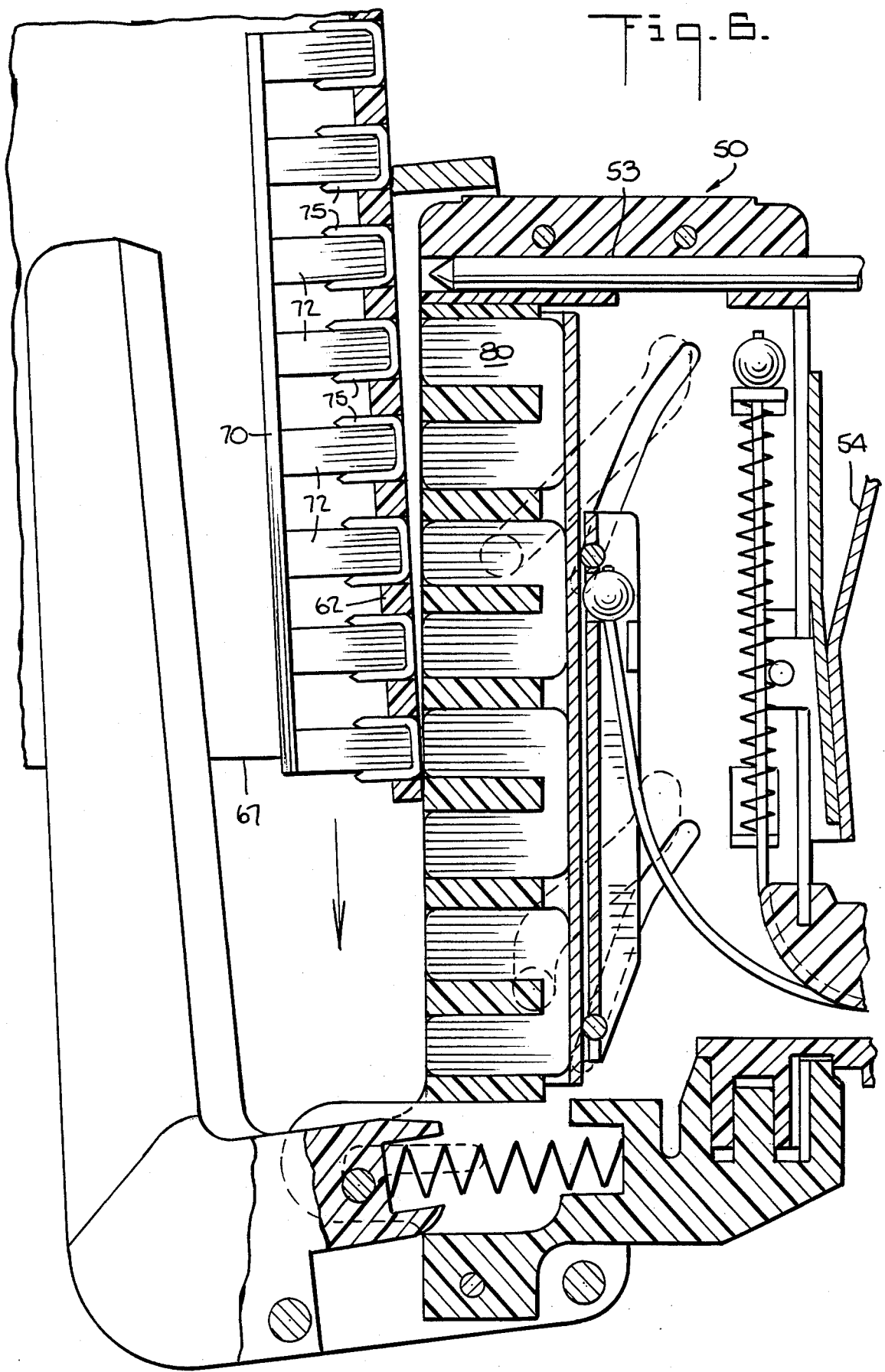
FIG. 6 is an enlarged side elevation view, partially in cross-section, depicting the reloading unit of the present invention being inserted into the open spent staple cartridge of a surgical fastening instrument.

When the instrument is ready to be reloaded, the instrument is placed in the open position, i.e., the anvil portion 51 and staple cartridge 52 are in spaced relation, and reloading unit 60 is inserted as depicted in FIG. 6 with the opening 67 in housing 61 being inserted over anvil portion 51. Loading is preferably accomplished by sliding reloading unit 60 along the empty staple cartridge 52 of the stapling assembly 50. Guide rails 64 are thus provided and spaced from one another a distance to accommodate the width of the staple cartridge 52. With the reloading unit 60 fully inserted within the open jaws of stapling assembly 50, as illustrated in FIG. 7, aperture 65 provided in holding plate 62 is in alignment with pin 53. Thus, insertion of the reloading unit 60, utilizing guide rails 64 and the alignment aperture 65, assures proper mating of the staples in reloading unit 60 with the empty staple cartridge 52. In the alternate embodiment using a removable housing, the housing is removed from the pusher bar 70 and holding plate 62 prior to insertion of the reloading unit.

Reloading of stapling assembly 50 is accomplished by first closing clamp actuator 20 which causes the alignment pin 53 to pass through the aperture 65 and which moves the anvil 51 of stapling assembly 50 into a bearing relationship with rear wall of the pusher member 70. Each of the staples 75 in reloading unit 60 is thus transferred to the empty array of openings in the staple carrying portion 51 of cartridge 50. In this manner, anvil 51 is urged against pusher member 70 and holding plate 62 is held in position against staple cartridge 52 of stapling assembly 50. Closure of the stapling assembly 50 causes pusher member 70, which is slidable with respect to holding plate 62, to push the staples 75 through apertures 63 in holding plate 62 and into the empty receptacles 80 in the staple cartridge 52. Simultaneously with loading a new charge of staples into staple cartridge 52, instrument 10 is set for firing.

In reloading the instrument, the U-shaped staples 75 are inserted into the empty receptacles 80 of staple cartridge 52 with the base or transverse leg of U-shaped staple 75 entering first. This is accomplished by the pusher bar teeth 72 bearing against the rear flat portion of staple 75 resulting in the pointed ends of staple 75 entering the staple cartridge 52 last. In order to properly reload instrument 10, it is important to shape the teeth 72 substantially to conform to the inner portions of staple 75 and be of a length sufficient to insure proper insertion of the staple. In this respect, teeth 72 on pusher member 70 are of a length sufficient to cause the inserted staple 75 to have its legs inserted below the surface of staple cartridge 52. Insertion to this depth will insure that the staples do not tear or bruise the skin as it is inserted into the jaws of the stapling assembly 50 during a surgical procedure.

Utilization of the reloading unit 60 with a surgical instrument, such as the described linear surgical fastener 10, substantially reduces the effective cost for multiple stapling procedures on a single patient. Moreover, the procedure of reloading the instrument may be accomplished effectively and quickly without any cumbersome technique. Thus, the reloading unit of the present invention is ideally suited for use in surgical procedures.

It is recognized that although the above description is directed to a preferred embodiment of the invention, it is noted that other variations and modifications will be apparent to those skilled in the art and, therefore, may be made without departing from the spirit and scope of the present disclosure.

What is claimed is:

1. A transfer magazine for providing a charge of staples to a staple cartridge in a surgical fastening instrument which comprises:
   pusher means having a plurality of staple support members spaced from one another, each of said support members being generally shaped to conform to the inner surface of a staple;
   a plurality of staples disposed on said staple support members, and
   holding means having therein a plurality of receptacles adapted to mate with and hold each of said staples on said support members prior to transfer to the staple cartridge, said holding means being adapted to slidably move with respect to said staples and support members to release said staplers held therein and facilitate loading a charge of staples into the staple cartridge of the surgical fastening instrument.

2. A transfer magazine in accordance with claim 1 wherein said pusher means includes a stop member disposed adjacent the end of said staple support members opposite the staple bearing end so as to limit the movement of said pusher means with respect to said holding means.

3. A transfer magazine in accordance with claim 1 wherein said holding means includes on each side thereof a guide rail for slidably engaging side edges of the staple cartridge in the surgical fastening instrument.

4. A transfer magazine in accordance with claim 1 wherein said surgical fastening instrument includes an alignment pin thereon between the staple cartridge and anvil, and which further includes on said holding means an aperture for mating with the alignment pin on said surgical fastening instrument to effect alignment of the charge of staples in said transfer magazine with said staple cartridge thereby allowing for transfer of the new charge of said staples in said transfer magazine to said staple cartridge upon closure of said surgical fastening instrument.

5. A transfer magazine in accordance with claim 1 wherein said pusher means comprises a comb-like bar having each of said staple support members interconnected to one another at the rearward end thereof, said rearward end thereby acting as a stop means with respect to limiting slidable engagement with said holding means.

6. A transfer magazine in accordance with claim 1 which further includes housing means covering said pusher means and the rear surface of said holding means.

7. A transfer magazine in accordance with claim 6 wherein said housing means including an indicator opening at least one side wall thereof to facilitate viewing said pusher means to ascertain whether said transfer magazine includes a charge of staples therein.

8. A transfer magazine in accordance with claim 1 wherein said staple support members are of length sufficient to reload staples into the staple cartridge to a depth such that the staple ends do not protrude through the surface thereof.

9. A reloading unit for use with surgical fastening instruments having staple cartridges to provide a new charge of staples to said cartridge and reload said instrument thereby enabling reuse thereof in surgical procedures which comprises:
pusher means in the form of a comb-like member including a plurality of spaced prongs which serve as staple support members and generally conform to the inner shape of a staple;
a plurality of U-shaped staples disposed over said staple support members;
holding means having therein a plurality of receptacles adapted to hold and slidably engage said staples disposed over said support members;
guide means disposed on said holding means for slidably engaging the side edges of the staple cartridge on the surgical fastening instrument; and
alignment means for aligning the charge of staples in said transfer magazine with said staple cartridge to allow for transfer of the new charge of said staples in said transfer magazine to said staple cartridge upon closure of said surgical fastening instrument.

10. A reloading unit in accordance with claim 9 which further includes housing means for enclosing said pusher means and receiving means, said housing means including therein indicator means to permit viewing of said pusher means to determine if said reloading unit includes a charge of staples therein.

11. A method of performing multiple stapling functions utilizing a stapling instrument which comprises the steps of:
firing the instrument to expend a charge of staples contained in a staple cartridge of the instrument;
providing a new charge of staples in a transfer magazine for reloading said staple cartridge, said transfer magazine including therein a plurality of staples corresponding substantially to the number of staples carried in said staple cartridge;
opening the instrument to separate the staple cartridge and anvil portions of the stapling assembly;
positioning said transfer magazine between the open portions of said stapling assembly;
aligning said transfer magazine and staple cartridge to facilitate transfer of said staples in said magazine to said cartridge with a closed end of each of said plurality of said staples first entering said cartridge thereby aligning the free end of the legs of the staple with the opening in said cartridge; and
closing said surgical instrument sufficiently to cause said staple cartridge and anvil portions of said stapling assembly to close upon said transfer magazine disposed therebetween so as to cause transfer of the staples from said transfer magazine to said staple cartridge.

12. The method of claim 11 wherein said aligning step includes the step of extending a pin member through said stapling assembly and said transfer magazine upon closure of said instrument.

13. The method of claim 11 wherein said positioning step includes the step of guiding said transfer magazine with respect to the staple cartridge portion of said stapling assembly by means of rail members disposed on said transfer magazine.

14. The method of claim 11 wherein said closing step includes urging a pusher member in said transfer magazine against the inner portion of said charge of staples thereby causing said staples to be transferred to the openings in said staple cartridge.

15. The method of claim 14 wherein said closing step includes the step of inserting said staples into said staple cartridge sufficiently to prevent the protrusion of the staple ends through the surface thereof.

* * * * *

UNITED STATES PATENT AND TRADEMARK OFFICE
CERTIFICATE OF CORRECTION

PATENT NO. : 4,714,187

DATED : December 22, 1987

INVENTOR(S) : David T. Green

It is certified that error appears in the above-identified patent and that said Letters Patent is hereby corrected as shown below:

Column 2, line 27, between "form" and "a" insert --of--.

Column 6, line 55, delete "staplers" and insert therefor --staples--.

Signed and Sealed this

Twenty-first Day of March, 1989

Attest:

DONALD J. QUIGG

*Attesting Officer*   *Commissioner of Patents and Trademarks*